(12) United States Patent
Godbole

(10) Patent No.: US 11,798,226 B2
(45) Date of Patent: *Oct. 24, 2023

(54) METHOD FOR GENERATING A CUSTOM BODY PART BRACE FOR A PATIENT

(71) Applicant: Able Hands Rehab PC, Old Bridge, NJ (US)

(72) Inventor: Shirish Godbole, Freehold, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/683,994

(22) Filed: Mar. 1, 2022

(65) Prior Publication Data

US 2022/0262065 A1 Aug. 18, 2022

Related U.S. Application Data

(63) Continuation of application No. 17/334,293, filed on May 28, 2021, now Pat. No. 11,295,513.
(Continued)

(51) Int. Cl.
*G06T 15/00* (2011.01)
*G06T 15/20* (2011.01)
(Continued)

(52) U.S. Cl.
CPC .......... *G06T 15/205* (2013.01); *B29C 64/393* (2017.08); *B33Y 50/02* (2014.12);
(Continued)

(58) Field of Classification Search
CPC ....... B33Y 50/00; B33Y 50/02; B29C 64/393; G16H 30/40; G16H 20/30; G16H 50/50; G06Q 30/0283; G06Q 30/0621; G06T 15/205; G06T 19/20; G06T 17/20; G06T 2219/2021; G06T 2210/41;
(Continued)

(56) References Cited

U.S. PATENT DOCUMENTS 6,102,880 A 8/2000 Nelson et al.
6,552,729 B1 4/2003 Di Bernardo et al.
(Continued)

OTHER PUBLICATIONS

CNC Kichen, How Much do 3D printed parts really Cost?, Oct. 8, 2017; https://www.youtube.com/watch?v=ffg9dArNfCg.*
(Continued)

*Primary Examiner* — Phu K Nguyen
(74) *Attorney, Agent, or Firm* — Lerner David LLP

(57) ABSTRACT

A computer-based method for generating a custom hand brace for a patient includes compiling optical data captured during a three-dimensional scan of a target hand of the patient into a three-dimensional hand model of the target hand; and receiving a diagnosis for an injury to the target hand of the patient. Based on the diagnosis, the method includes generating a custom hand brace model by extracting a first set of points from the three-dimensional hand model to generate an initial hand brace model; forming an interior surface of the initial hand brace model based on the first set of points; deforming the interior surface of the initial hand brace model into alignment with an exterior surface of the three-dimensional hand model to generate the custom hand brace model; and queuing the custom hand brace model for fabricating at an advanced manufacturing system.

18 Claims, 5 Drawing Sheets

Related U.S. Application Data

(60) Provisional application No. 63/088,994, filed on Oct. 7, 2020.

(51) Int. Cl.

| | |
|---|---|
| *G06T 17/20* | (2006.01) |
| *G06T 19/20* | (2011.01) |
| *G06F 30/17* | (2020.01) |
| *B29C 64/393* | (2017.01) |
| *B33Y 50/02* | (2015.01) |
| *G06Q 30/0283* | (2023.01) |
| *G06Q 30/0601* | (2023.01) |
| *G06F 111/16* | (2020.01) |
| *G06F 113/10* | (2020.01) |

(52) U.S. Cl.
CPC ......... *G06F 30/17* (2020.01); *G06Q 30/0283* (2013.01); *G06Q 30/0621* (2013.01); *G06T 17/20* (2013.01); *G06T 19/20* (2013.01); *G06F 2111/16* (2020.01); *G06F 2113/10* (2020.01); *G06T 2219/004* (2013.01); *G06T 2219/2021* (2013.01)

(58) Field of Classification Search
CPC ........... G06T 2219/004; G06F 2111/16; G06F 2113/10; G06F 30/17
USPC ........................................................ 345/418
See application file for complete search history.

(56) References Cited

U.S. PATENT DOCUMENTS

| | | | |
|---|---|---|---|
| 7,499,048 B2 | 3/2009 | Sieracki et al. | |
| 8,928,671 B2 | 1/2015 | Adler et al. | |
| 8,963,914 B2 | 2/2015 | Rawat et al. | |
| 10,861,590 B2 | 12/2020 | White et al. | |
| 10,978,189 B2 | 4/2021 | White et al. | |
| 11,096,828 B2 | 8/2021 | George et al. | |
| 2014/0142486 A1* | 5/2014 | Summit ................ | A61F 5/0104 602/20 |
| 2015/0328016 A1 | 11/2015 | Summit et al. | |
| 2015/0374529 A1* | 12/2015 | Summit ................ | A61F 5/0118 602/5 |
| 2016/0374431 A1 | 12/2016 | Tow | |
| 2021/0022899 A1 | 1/2021 | Anunike | |
| 2022/0262065 A1* | 8/2022 | Godbole ................ | G16H 20/30 |

OTHER PUBLICATIONS

Sanz-Pena I, Arachchi S, Halwala-Vithanage D, Mallikarachchi S, Kirumbara-Liyanage J, McGregor A, Silva P, Newell N. Characterising the mould rectification process for designing scoliosis braces: Towards automated digital design of 3d-printed braces. Applied Sciences. May 19, 2021;11(10):4665.*

Cobetto N, Aubin CE Clin J, Le May S, Desblens-Blais F. Labelle H, Parent S. Braces Optimized With Computer-Assisted Design And Simulations Are Lighter, More Comfortable, And More Efficient Than Plaster-Cast Braces for the Treatment of Adolescent Idiopathic Scoliosis. Spine Deformity. Jul. 1, 2014;2(4): 276-84.

Zhang Y, Kwok TH. Customization and Topology Optimization of Compression Casts/Braces on Two-Manifold Surfaces. Computer-Aided Design. Jun. 1, 2019;111:113-22.

* cited by examiner

METHOD FOR GENERATING A CUSTOM BODY PART BRACE FOR A PATIENT

CROSS REFERENCE TO RELATED APPLICATIONS

This Application is a continuation of U.S. patent application Ser. No. 17/334,293, filed on May 28, 2021, which claims priority to U.S. Provisional Patent Application No. 63/088,994, filed on Oct. 7, 2020, which is are incorporated in its their entirety by reference.

TECHNICAL FIELD

This invention relates generally to the field of Physical and Occupational Therapy devices and more specifically to a new and useful method for generating custom hand splints or any custom splint/brace for upper and lower extremities for patients recovering in the field of Physical medicine and rehabilitation.

DESCRIPTION OF THE EMBODIMENTS

The following description of embodiments of the invention is not intended to limit the invention to these embodiments but rather to enable a person skilled in the art of three-dimensional scanning to make and use this invention. Variations, configurations, implementations, example implementations, and examples described herein are optional and are not exclusive to the variations, configurations, implementations, example implementations, and examples they describe. The invention described herein can include any and all permutations and combinations of these variations, configurations, implementations, example implementations, and examples.

1. Method

Figure 1:
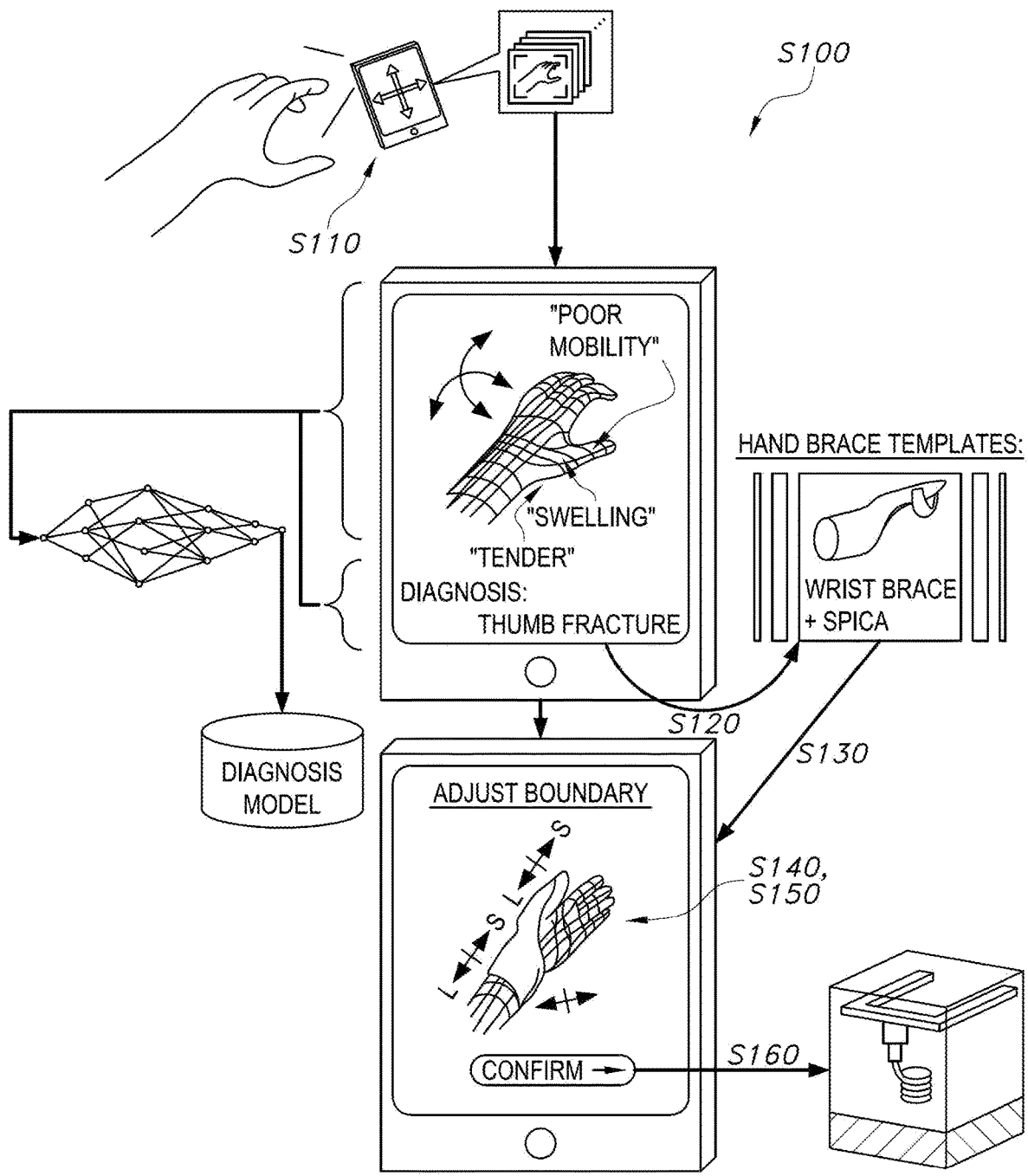
FIG. 1 is a schematic representation of one variation of a method.

As shown in FIG. 1, a method S100 for generating a custom hand brace for a patient includes: compiling optical data captured during a three-dimensional scan of a target hand of the patient into a three-dimensional hand model of the target hand in Block S110; receiving selection of a hand brace type, from a set of hand brace types, from a user in Block S120; retrieving a template brace model for the hand brace type in Block S130; aligning the template brace model to the three-dimensional hand model in Block S140; deforming an interior surface of the template brace model into alignment with an exterior surface of the three-dimensional hand model to calculate a custom hand brace model in Block S150; and queuing the custom hand brace model for fabricating at an advanced manufacturing system in Block S160.

One variation of the method S100 for generating a custom hand brace for a patient includes: compiling optical data captured during a three-dimensional scan of a target hand of the patient into a three-dimensional hand model of the target hand at a computing device in Block S110; and receiving a diagnosis for an injury to the target hand of the patient at the computing device in Block S111. Based on the diagnosis, the method includes generating a custom hand brace model at the computing device in Block S112 by: extracting a first set of points from the three-dimensional hand model to generate an initial hand brace model in Block S113; forming an interior surface of the initial hand brace model based on the first set of points in Block S114; deforming the interior surface of the initial hand brace model into alignment with an exterior surface of the three-dimensional hand model to generate the custom hand brace model in Block S150; and queuing, at the computing device, the custom hand brace model for fabricating at an advanced manufacturing system in Block S160.

Another variation of the method S100 for generating a custom hand brace for a patient includes compiling optical data captured during a three-dimensional scan of a target hand of the patient into a three-dimensional hand model of the target hand at a computing device in Block S110. The method further includes receiving injury data for the target hand of the patient on the three-dimensional hand model at the computing device in Block S115 by: rendering the three-dimensional hand model on a display of the computing device; receiving user input defining a set of markers on the three-dimensional hand model via the display of the computing device in Block S116; displaying an annotation menu of injury data for each marker; and for each marker in the set of markers, receiving a selection of an annotation from the annotation menu via the display of the computing device in Block S117. The method further includes: predicting an injury type based on the injury data at the computing device in Block S118; retrieving a hand brace type, from a set of hand brace types, based on the predicted injury type at the computing device in Block S120; retrieving a template brace model for the hand brace type at the computing device in Block S130; overlaying the template brace model onto the three-dimensional hand model at the computing device in Block S140; deforming the template brace model into alignment with the three-dimensional hand model to calculate a custom hand brace model at the computing device in Block s150; and queuing, at the computing device, the custom hand brace model for fabricating at an advanced manufacturing system in Block S160.

Yet another variation of method S100 for generating a custom hand brace for a patient includes retrieving a three-dimensional hand model of a target hand of the patient at a computing device in Block S110. The method further includes receiving injury data for the target hand of the patient on the three-dimensional hand model at the computing device in Block S115 by: rendering the three-dimensional hand model on a display of the computing device; receiving user input defining a set of markers on the three-dimensional hand model via the display of the computing device in Block S116; displaying an annotation menu of injury data for each marker; for each marker in the set of markers, receiving a selection of an annotation from the annotation menu via the display of the computing device in Block S117; and predicting an injury type based on the injury data at the computing device in Block s118. Based on the predicted injury type, the method includes generating a custom hand brace model at the computing device in Block S112 by: extracting a first set of points from the three-dimensional hand model to generate an initial hand brace model in Block S113; forming an interior surface of the initial hand brace model based on the first set of points in Block S114; deforming the interior surface of the initial hand brace model into alignment with an exterior surface of the three-dimensional hand model to generate the custom hand brace model in Block S150; and queuing, at the computing device, the custom hand brace model for fabricating at an advanced manufacturing system in Block S160.

2. Applications

Generally, a native application executing on a user's mobile computing device (e.g., a smartphone, a tablet) and/or a remote computer system (e.g., a computer network, remote servers) can execute Blocks of the method S100 to: compile optical data—including three-dimensional photographic images, stereoscopic images, and/or depth maps—during a three-dimensional scan of a patient's hand; generate a three-dimensional model of the patient's hand based on the optical data; generate a custom hand brace model configured to support a type of injury diagnosed or predicted in the patient's hand; and to queue the resulting custom hand brace model for fabricating at an advanced manufacturing system (e.g., three-dimensional printing) to create a custom hand brace matched to the patient's anatomy and physiology and a diagnosed or predicted injury.

By generating a three-dimensional model of a patient's hand, the native application can: customize a hand brace that securely fits the patient's hand and provides the particular support needed for the patient's injury type, thus enabling the patient's hand to heal and recover in a stable manner without unnecessarily limiting the patient's dexterity or fine motor skills. Most off-the-shelf braces (such as those purchased at a pharmacy or grocery store) can be too wide, long, rigid, or flexible in various sections of the brace to provide suitable support for a patient's hand injury and prevent further injury to the patient's hand. The native application can analyze the anatomical features of a patient's hand and the injury type and/or diagnosis to generate a custom hand brace according to a patient's particular needs.

Furthermore, the native application can directly interface with a manufacturing system to quickly produce and deliver the custom hand brace to the patient, such that the patient can conveniently and efficiently obtain a custom hand brace without requiring the patient to visit a hospital or wait for several hours and/or days to see a doctor, receive a prescription for a medical-grade brace, and then wait additional days and/or weeks for the prescription to be approved by a medical insurance company and/or filled by a medical supply company.

2.1 Physician-Driven Hand Brace

In one example, a physician can facilitate the creation of a custom hand brace for a patient who has sustained a hand injury. In particular, Blocks of the method S100 can be implemented by a native application executing on a physician's (or therapist's) computing device to: guide the physician in scanning a patient's hand, entering a diagnosis for injury to the hand, and selecting or prescribing a hand brace type; generating a custom hand brace model for the patient based on these data; and queuing fabrication of a custom hand brace for the patient according to the custom hand brace model when confirmed by the physician. In this example, the native application and/or the remote computer system can also: interface with the patient to capture types, locations, and magnitudes of pain, swelling, and/or reduced mobility (and/or open wounds, deformities, hardware, deformities, etc.) in the patient's hand; fuse these patient-reported data with the physician's diagnosis; and derive a diagnosis model linking such patient-reported data to hand injury diagnoses based on a population of such diagnosis-labeled patient-reported data. Additionally or alternatively, the native application and/or the remote computer system can: fuse patient-reported data with hand brace types and configurations selected by physicians or therapists, etc.; and derive a hand brace type model linking such patient-reported data to a type of hand brace based on a population of such diagnosis-labeled patient-reported data.

Accordingly, the physician can: evaluate the patient's hand in-person; determine a diagnosis for the patient's hand injury; leverage a database of prior diagnoses and/or a database of template brace models to generate a custom hand brace model for the patient; and, via a user interface on the physician's computing device, render the custom hand brace model on the user interface and further modify the custom hand brace model to suit the patient's particular needs. The physician can then queue the custom hand brace for printing at an advanced manufacturing system located within the clinic and/or hospital, such that the patient can try on the custom hand brace before leaving the appointment, or at an advanced manufacturing system at a remote location, such that the custom hand brace is delivered to a home address of the patient.

2.2 Consumer-Driven Hand Brace

In another example, a user can generate her own custom hand brace without visiting a hospital or scheduling a doctor's appointment after sustaining a hand injury. The native application can interface with a user directly to: generate a three-dimensional hand model of the user's hand based on scan data collected by the user's computing device; capture types, locations, and magnitudes of pain, swelling, and/or reduced mobility in the user's hand; leverage these user-reported data and the diagnosis model and/or the hand brace type model to diagnose an injury to the user's hand and to select a hand brace type for the user, such as for immobilization as a first line of treatment to the hand; retrieve a template brace model of this type; deform the template brace model into alignment with the three-dimensional hand model of the user's hand; and to queue the resulting custom hand brace model for additive manufacture (e.g., three-dimensional printing) for rapid production and delivery of a custom hand brace matched to the user's physiology.

Accordingly, the user can: scan her own hand to create a three-dimensional hand model; annotate the three-dimensional hand model with injury data; leverage a database of prior diagnoses and/or a database of template brace models to generate a custom hand brace model; and confirm an order for the production of the custom hand brace and delivery to her home address (or pick-up at a designated local store). By interfacing with the native application on her computing device, the user can quickly and conveniently obtain a custom hand brace for her hand injury, particularly for any injury occurring during hours with limited access to a clinic and/or a doctor (e.g., on weeknights and/or weekends) or while in a remote location (e.g., on a camping or hiking trip) without nearby medical access.

Therefore, the native application and/or the remote computer system can implement Blocks of the method S100 to generate a custom three-dimensional hand model for rapid production and delivery of a custom hand brace as a treatment matched to a user's physiology based on limited scan, diagnosis, and/or user-reported symptom data.

Blocks of the method S100 are described herein as executed by a native application executing on a user's computing device, such as smartphone or tablet. However, Blocks of the method S100 can additionally or alternatively be executed within a web browser, native application, or other application or process executing on a mobile device, a dedicated hand scanner, and/or any other computing device. Blocks of the method S100 can interface with an advanced manufacturing system—including additive manufacturing systems (e.g., 3D printing), computer numerical control (CNC) systems, casting and/or molding systems—to manufacture the custom hand brace.

Furthermore, the method S100 is described herein to generate a custom hand brace for a human hand. However, the method S100 can additionally or alternatively be executed to generate a custom brace for an arm, back, knee, ankle, neck, and/or other human body part, such as prescribed by a physician or for self-treatment by a user. The method S100 can additionally or alternatively be executed to generate a custom brace for another animal, such as a dog, cat, or horse, etc.

3. System

Figure 2:
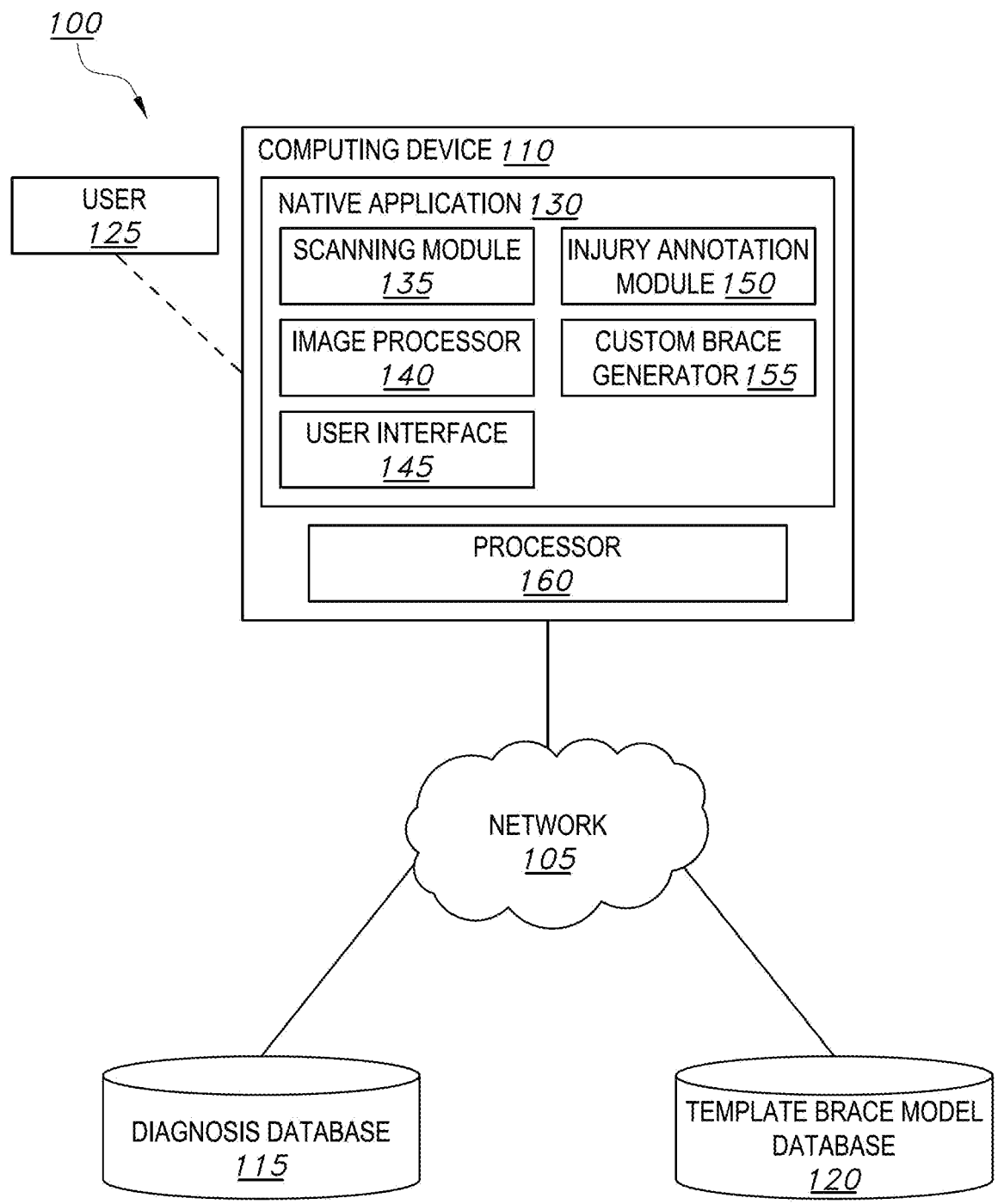
FIG. 2 is a system environment for executing the method.
Figure 3:
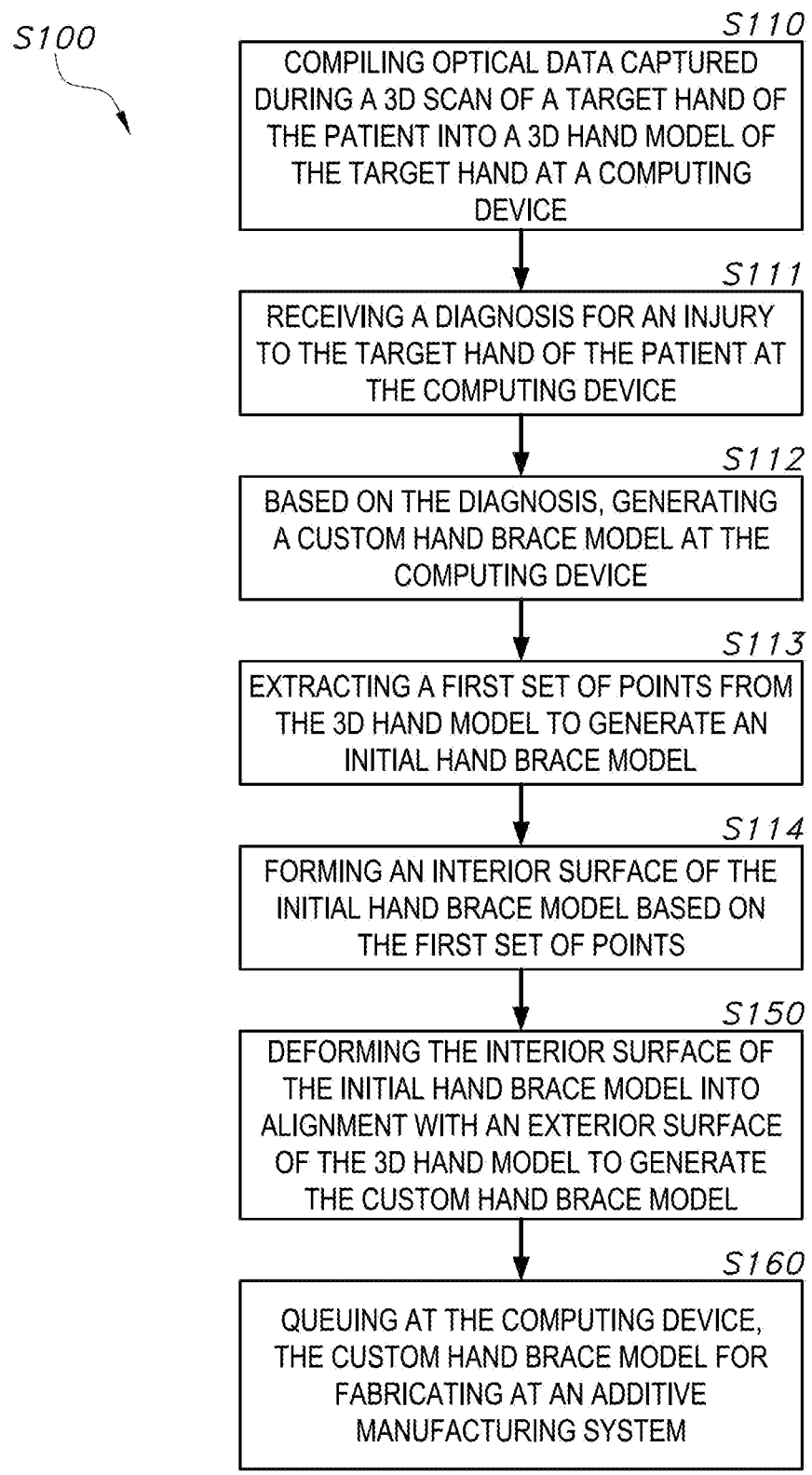
FIG. 3 is a flowchart representation of one variation of the method.
Figure 4:
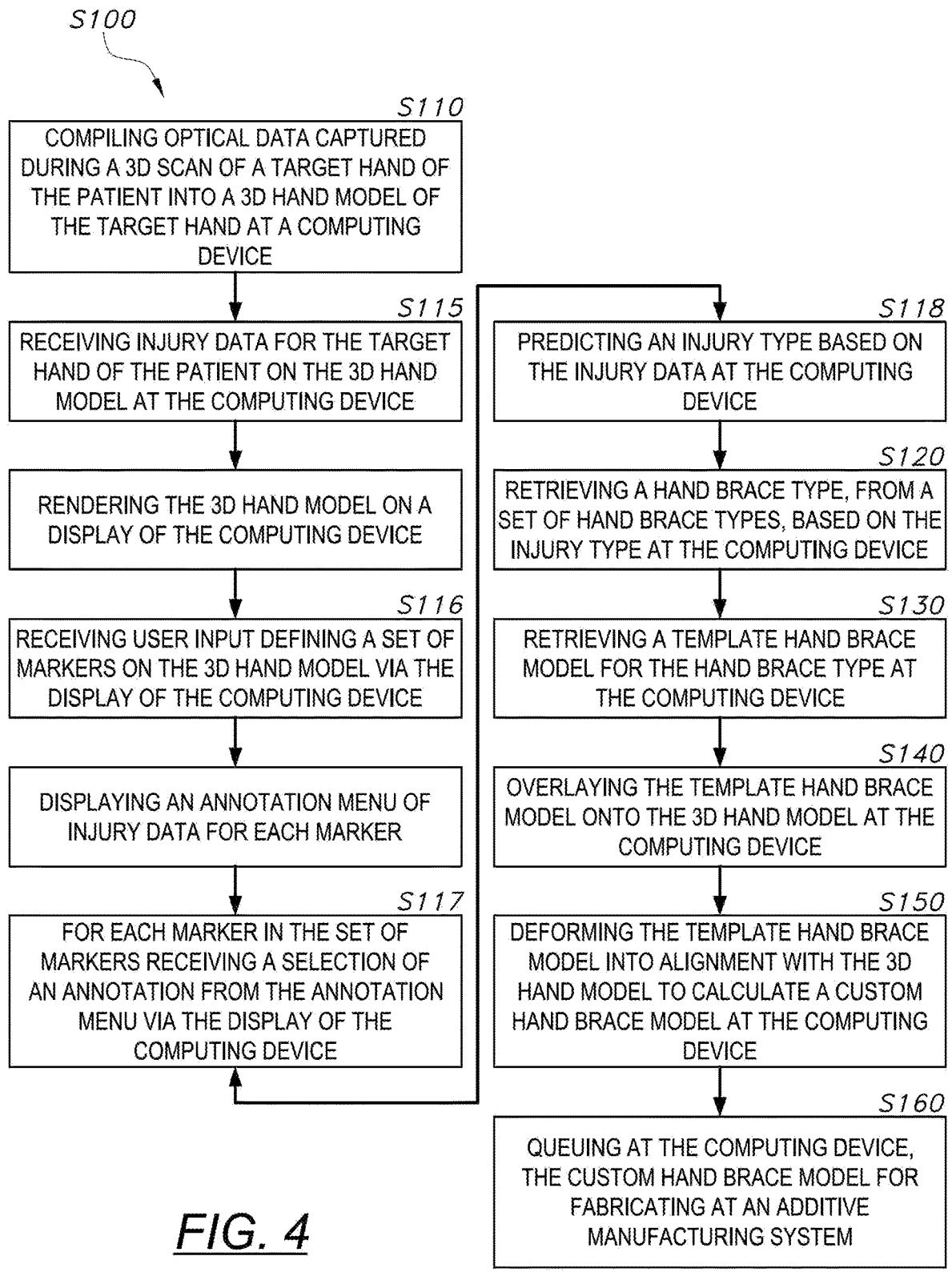
FIG. 4 is a flowchart representation of another variation of the method.
Figure 5:
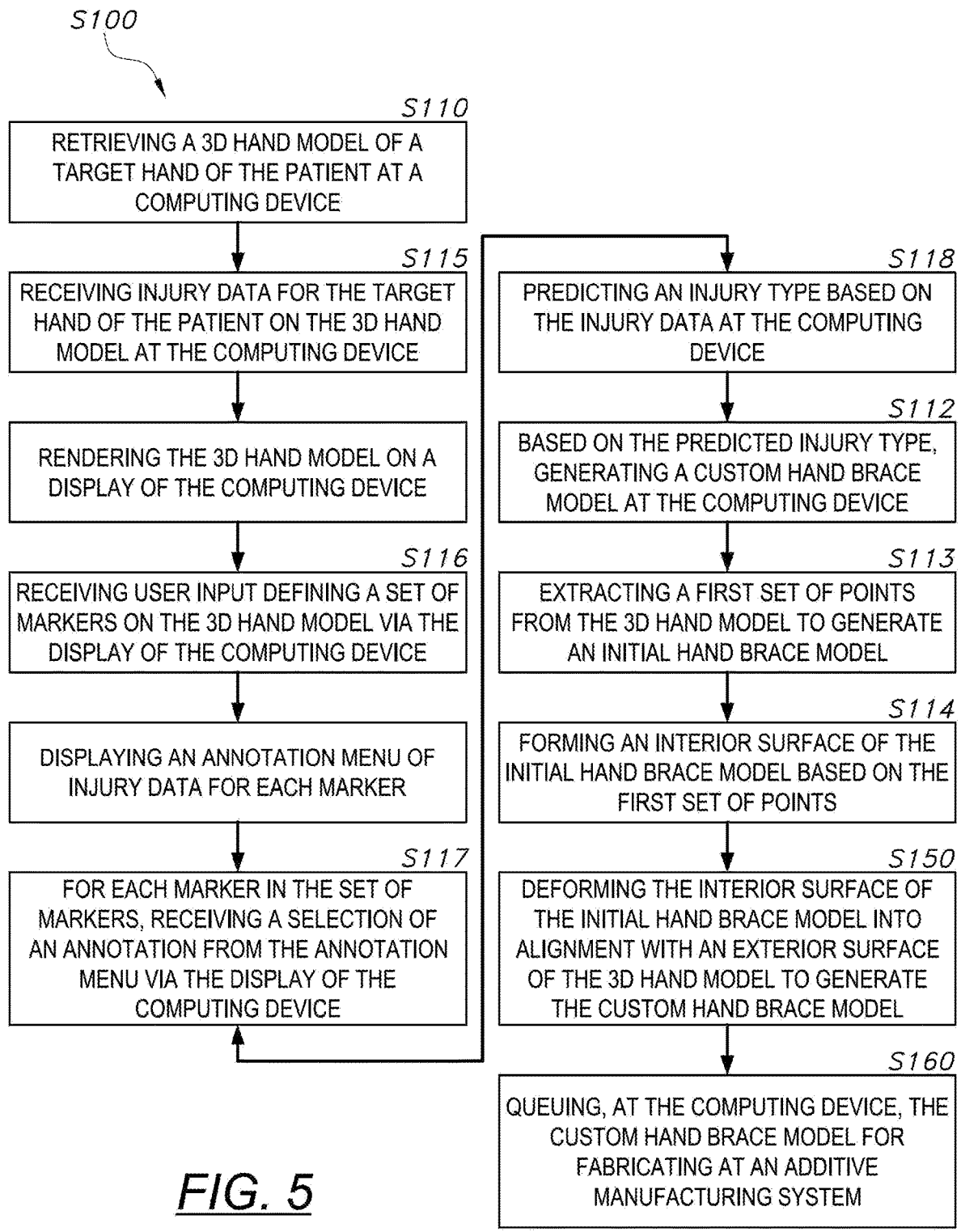
FIG. 5 is a flowchart representation of yet another variation of the method.

As shown in FIG. 2, a system 100 can generate a custom hand brace model for a patient with a particular hand injury. The system 100 can include a network 105 (e.g., wireless, LAN, WAN, etc.) that connects a set of computing devices 110 (e.g., a mobile device, a computer, a dedicated hand scanner) to a diagnosis database 115 and a template brace model database 120. The diagnosis database 115 can store diagnoses of hand injuries of prior patients that the system 100 can then leverage to determine a diagnosis of the particular hand injury for the patient. The template brace model database 120 can store a set of template brace models that each correspond to a hand injury type (or a particular combination of hand injury types) and can be further customized for the particular hand injury of the patient.

A user 125 (e.g., physician, nurse, therapist, patient) can interface with a computing device no to input patient data (e.g., personal information, medical history, injury data, diagnosis), scan a target hand of the patient, and customize a hand brace model for the patient. The computing device 110 can include a processor 160 that cooperates with memory and storage modules of the computing device 110 to execute computer-implemented methods and instructions via software, including a native application 130 configured to execute Blocks of the method S100. The native application 130 can include a scanning module 135, an image processor 140, a user interface 145, an injury annotation module 150, a custom brace generator 155, and a processor 160.

The scanning module 135 can scan a patient's hand—for example via a camera associated with or integrated into the computing device 110—to capture a set of three-dimensional photographic images, stereoscopic images, and/or depth maps of the patient's hand and record concurrent motion data, such as from an IMU integrated into the computing device.

The image processor 140 can process the set of three-dimensional photographic images, stereoscopic images, and/or depth maps of the patient's hand to assemble the set of images into a three-dimensional representation of a scan volume—including the patient's target hand and the surrounding field—and segment the three-dimensional hand model from the scan volume.

The user interface 145 can display the three-dimensional hand model of the patient's hand based on the set of images and receive user input to annotate, customize, and/or modify various features of the three-dimensional hand model (e.g., a proximal forearm section, a distal thumb section, distal second and third phalange sections, and distal fourth and fifth phalange sections).

The injury annotation module 150 can receive patient-reported injury data via the user interface 145 by prompting the user to indicate pain areas on the three-dimensional hand model and to annotate pain magnitudes and pain types.

The custom brace generator 155 can generate a model of a custom brace for a patient (e.g., based on patient-reported injury data and/or a physician diagnosis). In one implementation, the custom brace generator 155 can retrieve a template brace model from the template brace model database 120 and customize the template brace model based on the particular hand injury type of the patient and/or anatomical features of the patient's target hand. In another implementation, the custom brace generator 155 can derive an initial hand brace model from the three-dimensional hand model of the patient (rather than retrieving a template) and modify the initial hand brace model to generate the custom brace for the patient.

4. Template Brace Models

In one implementation, the native application or a remote database (e.g., the template brace model database 120) stores a set of template brace models. In this implementation, each template brace model: corresponds to a particular hand injury type (or a particular combination of hand injury types); includes a specification for a particular hand brace print material (e.g., a rigid polymer, an elastic or flexible polymer, or low-temperature formable thermoform polymer); and a specification for types and locations of stays (e.g., hook-and-loop straps, elastic bands). Each template brace model also includes a three-dimensional model (e.g., in the form of a solid CAD model, a surface CAD model, a CAD mesh) defining: support structures for a forearm, wrist, palm, and/or fingers according to the particular hand injury associated with the template hand brace; apertures for fingers not necessitating support according to the particular hand injury; variations in wall thickness as a function of the specified material, target elasticity in particular locations as prescribed by the particular hand injury, and target rigidity in other locations as prescribed by the particular hand injury; integral loops or pass-throughs for stays; and/or integral flats for bonding or adhering stays.

In this implementation, a three-dimensional model within a template brace model can also define a set of snap points located on (or relative to) the interior surface of the three-dimensional model and configured to snap to key features on a three-dimensional hand model generated from a scan of a patient's hand. For example, a three-dimensional model within a template brace model can include: one snap point per fingertip; one snap point per interphalangeal joint; one point for an ulnar styloid process; and one point for a radial styloid process.

In this implementation, the set of template brace models can include: a wrist brace template model associated with RSI pain, Carpal Tunnel, or gamer wrist; a wrist brace with a thumb spica template model associated with De Quervain's Tenosynovitis, ligament instability, thumb injuries, and muscle strains; a short thumb spica template model associated with injury to the ulnar collateral ligament, injury to the proximal first phalanx or distal first metacarpal, and severe sprains of the thumb; a wrist brace with a long thumb spica template model associated with thumb fracture; a radial gutter fracture brace template model configured to support the second and/or third metacarpal bones and respective metacarpal-phalangeal joints; an ulnar deviation/drift hand splint template model associated with arthritis and MCP knuckle joint support; a short arm fracture brace template model associated with fractures and acute injuries of the distal radius and/or distal ulna; a long thumb splint (with or without boa) template model associated with injuries to the base of the thumb (e.g., Bennett's and Rolando's fractures), navicular fractures, and injuries to the trapezium or trapezoid bones of the wrist; a hand-based radial ulnar gutter brace template model associated with fractures to the second and/or third metacarpals and/or phalanges; a hand-based ulnar radial gutter brace template model associated with fractures to the fourth and fifth metacarpals and/or phalanges; and a boxer's fracture brace template model.

5. Custom Physician-Driven Hand Brace

In one configuration shown in FIG. 1, a user (e.g., physician, therapist) interfaces with the native application—executing on a computing device—to create a custom hand brace model for a patient and to confirm manufacture of a custom brace for the patient according to this custom hand brace model.

5.1. Diagnosis

In this configuration, the user interfaces with the patient and/or reviews radiographic images, etc. to diagnose an injury to the patient's hand (hereinafter the "target hand"). The user then: opens the native application on a computing device; enters patient identification data or connects a medical record of the patient; and initiates a new brace order for the patient.

The native application can then: prompt the user to specify diagnosis details of the injury, such as a primary injury type, a primary injury magnitude, a secondary injury type, a secondary injury magnitude, and polarity of the target hand (i.e., the patient's left or right hand); and populate the new brace order with these data.

In one implementation, the native application can: isolate a subset of hand brace types affiliated with the primary injury type (and/or the second injury type, etc.) diagnosed by the user; present this subset of hand brace types to the user; and prompt the user to select a particular hand brace type from this subset of hand brace types.

In another implementation, the native application can: prompt the user to select a particular hand brace type from the set of available hand brace types, such as by selecting from a dropdown menu of these hand brace types; and then prompt the user to confirm that the patient presents all or a subset of the injury types associated with the selected hand brace type. In this implementation, the native application can also prompt the user to indicate a magnitude of each confirmed injury type and/or confirm a polarity of the target hand.

5.2 Scan

The native application can then initialize an optical scan of the target hand and guide the user.

In one implementation shown in FIG. 1, during the scan, the patient places the target hand (and forearm) on a support surface (e.g., a pillow or flat table) and the user draws the computing device around the target hand according to instructions rendered by the native application. During this scan, the native application captures: optical data of the target hand including photographic images, stereoscopic images, and/or depth maps; and concurrent motion data, such as from an IMU integrated into the computing device.

During this scan, the native application can also: track the position and orientation of the computing device in space; predict regions of a three-dimensional hand model of the target hand, reconstructable from data captured by the computing device when occupying these past positions and orientations; predict remaining regions of the three-dimensional hand model of the target hand not yet reconstructable from data captured by the computing device; calculate additional positions and orientations of the computing device at which the computing device can capture data enabling reconstruction of remaining regions of the three-dimensional hand model; indicate these additional positions and orientations on the display of the computing device to guide the user toward completing the scan; and indicate to the user when sufficient data is collected to enable reconstruction of the three-dimensional hand model.

In this implementation, the native application can also: implement three-dimensional reconstruction techniques to locally assemble images captured by the computing device into a three-dimensional representation of the scan volume—including the target hand and the surrounding field—in real-time, such as based on orientations of the computing device when these images were captured and/or by aligning like pixel clusters in consecutive images; and then detect a hand and forearm in the three-dimensional representation of the scan volume, such as by implementing object recognition techniques and/or delineating a nonlinear volume in the three-dimensional representation of the scan volume as the hand and forearm (versus a planar background surface). In particular, the native application can compile optical data captured during this three-dimensional scan of the target hand of the patient into a three-dimensional hand model of the target hand at a computing device by assembling a set of photographic images captured of the target hand.

Alternatively, during or upon conclusion of the scan, the native application can: render the three-dimensional representation of the scan volume on the computing device's display; prompt the user to identify an object in the three-dimensional representation corresponding to the target hand; extract a three-dimensional volume of this object from the three-dimensional representation of the scan volume; and store this three-dimensional volume as the three-dimensional hand model of the target hand. Yet alternatively, the native application can upload images and device position and orientation data to the remote computer system, which then implements similar methods and techniques to generate the three-dimensional hand model of the target hand.

In another implementation, the native application can: implement three-dimensional reconstruction techniques to assemble images captured by the computing device into the three-dimensional model in real-time, such as based on orientations of the computing device when these images were captured and/or by aligning like pixel clusters in consecutive images; and render the current three-dimensional model on the display of the computing device in real-time—such as by overlaying a 2D projection of the three-dimensional model over and aligned to the like features in a viewfinder concurrently rendered on the display of the computing device—thereby enabling the user to visually discern missing scan data of the target hand.

However, the native application and/or the remote computer system can implement any other methods or techniques to generate a three-dimensional hand model of the target hand (and forearm) based on data collected by the computing device as the user manipulates the computing device about the target hand during the scan.

5.3. Brace Model

The native application (or the remote computer system) can then generate a custom hand brace model for the target hand of the patient.

5.3.1. Template Brace Model

In one implementation, the native application (or the remote computer system) can retrieve a template brace model for the hand brace type selected by the user, as shown in FIG. 1, and mirror the template brace model as necessary to match the template brace model to the polarity of the target hand.

The native application can also implement object recognition and/or object identification techniques (e.g., template matching) to identify key features—specified by the template brace model—on the three-dimensional hand model, such as each fingertip, each interphalangeal joint, the ulnar styloid process, and the radial styloid process. Alternatively, the native application can render the three-dimensional hand model on a display of the computing device, and, for each key feature in a set of key features on the three-dimensional hand model: transmit a prompt on the display of the computing device to label a key feature on the three-dimensional hand model (e.g., by rendering the prompt "tap the ulnar styloid"); receive a selection of a pixel location on the three-dimensional hand model via the display of the computing device; store the pixel location on the three-dimensional hand model as corresponding to the key feature; and repeat this process for the remaining key features in this set in order to populate these key features on the three-dimensional hand model.

The native application (or the remote computer system) can then: deform the template brace model to locate each snap point defined in the template brace model onto the surface of the three-dimensional hand model at its corresponding key feature; deform the remainder of the template brace model to locate the interior surface of the template brace model into contact with the surface of the three-dimensional hand model while preserving the wall thickness(es) defined in the template brace model; and store this deformed template brace model as a custom hand brace model for the patient.

In another implementation, the native application can: calculate a position and orientation of the template brace model that minimizes an error (e.g., a distance) between the interior surface of the template brace model and the exterior surface of the three-dimensional hand model. The native application can then: lock the template brace model at this position and orientation relative to the three-dimensional hand model; deform the remainder of the template brace model to locate the interior surface of the template brace model into contact with the surface of the three-dimensional hand model while preserving the wall thickness(es) defined in the template brace model; and store this deformed template brace model as a custom hand brace model for the patient.

In one example, the native application can iteratively: calculate a total error between the interior surface of an initial hand brace model (e.g., the template brace model or an intermediary brace model generated during a subsequent iteration) and the exterior surface of the three-dimensional hand model; and, in response to the total error falling below an error threshold, store the initial hand brace model as the custom hand brace model.

However, the native application, the remote computer system, or a human operator can implement any other method or technique to align the template brace model to the three-dimensional hand model of the target hand.

5.3.2 Custom-Generated Brace Model

In one variation, the native application (or the remote computer system) can derive an initial hand brace model from the three-dimensional hand model of the patient (rather than retrieving a template brace model) and modify the initial hand brace model to generate the custom brace for the patient.

In particular, the native application can: compile optical data captured during a three-dimensional scan of a target hand of the patient into a three-dimensional hand model of the target hand at a computing device; and receive a diagnosis for an injury to the target hand of the patient at the computing device. Based on the diagnosis, the native application can generate a custom hand brace model at the computing device by: extracting a first set of points from the three-dimensional hand model to generate an initial hand brace model; forming an interior surface of the initial hand brace model based on the first set of points; and deforming the interior surface of the initial hand brace model into alignment with an exterior surface of the three-dimensional hand model to generate the custom hand brace model.

In one implementation, the native application can deform the interior surface of the initial hand brace model into alignment with the exterior surface of the three-dimensional hand model based on a specified wall thickness for the custom hand brace model.

In one implementation, the native application can deform the interior surface of the initial hand brace model into alignment with the exterior surface of the three-dimensional hand model by iteratively: calculating a total error between the interior surface of the initial hand brace model and the exterior surface of the three-dimensional hand model; and, in response to the total error falling below an error threshold, storing the initial hand brace model as the custom hand brace model.

5.4 Custom Hand Brace Model Manual Adjustment

The native application can also receive input from the user via the computing device to define the boundary of the custom hand model.

5.4.1 Brace Boundary

In one implementation shown in FIG. 1, the native application renders the custom hand brace model alongside a set of the sliders pointing to and configured to virtually extend and retract corresponding sections of the custom hand brace model.

More specifically, the native application can: render an initial hand brace model overlaid onto the three-dimensional hand model on a display of the computing device. For each phalange, in a set of phalanges, of the three-dimensional hand model, the native application can then: render a virtual slider along a length of the phalange and a corresponding section on the initial hand brace model; render a virtual pointer on the virtual slider; in response to user input adjusting a position of the virtual pointer along the virtual slider, adjust a length of the corresponding section on the initial hand brace model; and store the adjusted hand brace model as the custom hand brace model.

For example, the native application can: render the custom hand brace model overlayed over the three-dimensional hand model on the display of the computing device; render a set of virtual sliders adjacent the custom hand brace model, including one slider for each of a proximal forearm section, a distal thumb section, distal second and third phalange sections, and distal fourth and fifth phalange sections; render a virtual pointer between each slider and its corresponding section on the custom hand brace model; and update (i.e., increase or decrease) the length of each of these sections of the custom hand brace model rendered on the computing device responsive to manual adjustments of these sliders by the user.

In another implementation, the native application: prompts the user to manually draw a boundary line at the desired terminus of each of these sections directly on the custom hand brace model rendered on the display of the computing device; and retracts or extends these sections of the custom hand brace model to align with these manually-drawn boundary lines.

In a similar implementation, the native application can: enable the user to drag over each of these sections of the custom hand brace model directly on the display; and retract or extend these sections of the custom hand brace model accordingly.

In yet another implementation, the physician draws a desired boundary of the custom brace directly on the user's skin or bandages or casts, such as with a marker, prior to the scan. The native application (or the remote computer system) can thus: detect this marker line in the set of images captured by the computing device during the scan; project this line onto the three-dimensional hand model; and retract or extend sections of the custom hand brace model to align with this line thus projected onto the three-dimensional hand model.

5.4.2 Apertures

In a similar implementation, the physician defines apertures in the custom hand brace model (e.g., for surgical pins extending out of the user's skin), such as by drawing an aperture with a marker directly on the user's skin, drawing an aperture on the custom hand brace model within the native application, and/or "dropping" an aperture onto the custom hand brace model within the native application, etc. The native application can update the custom hand brace model to reflect these indicated apertures.

For example, the native application can: render an initial hand brace model overlaid onto the three-dimensional hand model on a display of the computing device; receive a selection of a pixel location on the initial hand brace model via the display of the computing device; receive an annotation defining an aperture at the pixel location on the initial hand brace model via the display of the computing device; update the initial hand brace model to define the aperture at the pixel location; and store the updated hand brace model as the custom hand brace model.

5.5 Custom Brace Confirmation

The native application can then render the custom hand brace model for review by the user and prompt the user to confirm production of a custom hand brace for the patient according to this custom hand brace model, as shown in FIG. 1.

The remote computer system (or the native application) can also: estimate a print time to create a custom hand brace based on the custom hand brace model; estimate a cost to fabricate the custom hand brace based on the print time and a size (e.g., length and/or volume) of the custom hand brace; and predict a delivery time for the custom hand brace based on a shipping address of the patient, the print time, and a predefined assembly time for the custom hand brace. The native application (and/or the remote computer system) can then: present the estimated cost and/or predicted delivery time on a display of the computing device; transmit a prompt to confirm an order for the custom hand brace via the display of the computing device; in response to receiving confirmation of the order, queue a three-dimensional printer to print the custom hand brace based on the custom hand brace model, as shown in FIG. 1; and queue the resulting custom hand brace for assembly and delivery to the patient.

In another implementation, the native application can render the custom hand brace model for review and transmit a prompt to confirm production of a custom hand brace for the patient at an advanced manufacturing system located within a clinic and/or store at which the patient is being evaluated, such that the patient can receive the custom hand brace before leaving the clinic and/or store. More specifically, the remote computer system (or the native application) can: estimate a print time to create a custom hand brace based on the custom hand brace model; estimate a cost to fabricate the custom hand brace based on the print time and a size (e.g., length and/or volume) of the custom hand brace; present the estimated cost on a display of the computing device; transmit a prompt to confirm an order for the custom hand brace via the display of the computing device; in response to receiving confirmation of the order, queue a three-dimensional printer to print the custom hand brace based on the custom hand brace model, as shown in FIG. 1; and queue the resulting custom hand brace for assembly for the patient.

5.6 Patient Symptoms and Autonomous Diagnosing Model

In one variation shown in FIG. 1, the native application can also interface with the patient directly or indirectly via the user (e.g., a relative assisting the patient) to collect self-reported symptoms of the injury from the patient.

In this variation, the native application can: render the three-dimensional hand model on the display of the computing device; prompt the patient to indicate pain areas on the three-dimensional hand model and to annotate types (e.g., sharp, dull, numb, throbbing, aching, pain only with movement, pain increase with movement) and magnitudes of pain at each pain area; prompt the patient to indicate areas of swelling on the three-dimensional hand model; and/or prompt the patient to indicate areas of reduced mobility on the three-dimensional hand model, such as reduction in range of motion in rotation of the forearm, articulation of the wrist, and articulation of each finger. For example, the native application can: render the three-dimensional hand model and on the display of the computing device; enable the user to place markers on discrete locations and over areas of the three-dimensional hand model; open a menu of pain, swelling, and mobility options for each marker; annotate each marker with pain, swelling, and/or mobility tags selected by the user, such as described above. More specifically, the native application can receive injury data for the target hand of the patient on the three-dimensional hand model at the computing device by rendering the three-dimensional hand model on a display of the computing device; receiving user input defining a set of markers on the three-dimensional hand model via the display of the computing device; displaying an annotation menu of injury data for each marker; and, for each marker in the set of markers, receiving a selection of an annotation from the annotation menu via the display of the computing device.

The native application (or the remote computer system) can thus link these pain, swelling, and/or mobility tags self-reported by the patient to discrete locations (e.g., individual joints, tendons) and regions (e.g., a wrist, a palm, a thumb) on the target hand in order to record self-reported spatially-located symptoms experienced by the patient given the injury type diagnosed by the user.

Additionally or alternatively, the native application can prompt the patient to complete a textual or graphical survey for presence and magnitude of pain, swelling, and mobility reduction throughout the target hand and forearm.

The remote computer system can then leverage these user and patient data to derive correlations between: such patient-reported pain areas, pain types, pain magnitudes, swelling, and/or mobility reduction; and hand injury diagnoses. For example, for each patient in a population of patients, the remote computer system can: retrieve patient-reported pain area, pain type, pain magnitude, swelling, and/or mobility reduction data and store these data in a multi-dimensional vector; and label the vector with an injury type (and/or a combination of injury types, an injury magnitude(s), etc.) diagnosed for this patient by a physician (or a therapist, etc.) concurrent with recordation of these patient-reported data. The native application can then aggregate such labeled vectors across a population of patients with diagnosed hand injuries and implement artificial intelligence, machine learning, regression, and/or other techniques to derive correlations between: combinations of patient-reported pain areas, pain types, pain magnitudes, swelling, and/or mobility reduction; and an injury type (or a combination of injuries, an injury magnitude(s), etc.). The remote computer system can store or represent these correlations in a diagnosis model (e.g., a neural network) that ingests patient-reported pain areas, pain types, pain magnitudes, swelling, and/or mobility reduction and returns a predicted injury type (and/or a predicted combination of injury types, a predicted injury magnitude(s), etc.).

Alternatively, the diagnosis model can be constructed prescriptively, such as manually by an operator and stored in a parametric model or a non-parametric model (e.g., a table, a set of template patient-reported injury symptoms).

However, the remote computer system (or an operator, etc.) can implement any other method or technique to generate a diagnosis model that links patient-reported symptoms to one or more possible injury types.

5.6.1 Brace Type Model

In the foregoing variation, the remote computer system can also link each hand brace type to one or more injury types (or combinations of injury types, injury magnitude ranges, etc.) predicted by the diagnosis model. The native application (or the remote computer system) can later: implement this diagnosis model to predict a particular type of hand injury to a new user based on patient-reported injury symptoms; and select a hand brace type linked to this particular type of hand injury for the new patient, as described below.

Alternatively, the remote computer system can implement similar methods and techniques to derive correlations between: combinations of pain areas, pain types, pain magnitudes, swelling, and/or mobility reduction reported by patients; and hand brace type, configuration of a hand brace type, and/or boundary profile of a hand brace type, etc. prescribed by physicians (and/or therapists, etc.). The remote computer system can then store these correlations in a brace type model (e.g., a neural network) that ingests patient-reported pain areas, pain types, pain magnitudes, swelling, and/or mobility reduction and returns a particular hand brace type, a configuration of the particular hand brace type, and/or boundary profile for the particular hand brace type predicted to match an injury type that yields such symptoms.

Therefore, the native application (or the remote computer system) can later implement this brace type model to select a particular brace type, a configuration of the particular hand brace type, and/or boundary profile for the particular hand brace based on injury symptoms reported by a new patient, as described below.

6. Custom Consumer-Driven Hand Brace

In another configuration, the native application calculates a custom hand brace for a user by interfacing directly with the user and sans input from a physician (or therapist, directly).

6.1 Scan and Three-Dimensional Hand Model

In this configuration, when the user opens the native application on her computing device and initiates a new brace order, the native application implements methods and techniques described herein to guide the user in manipulating the computing device around her injured hand (i.e., the target hand) while capturing images of the target hand. The native application (and/or the remote computer system, etc.) can then implement methods and techniques described herein to reconstruct a three-dimensional hand model of the target hand and to detect key features in the three-dimensional hand model.

6.2 Injury Self-Reporting

The native application can then: prompt the user to indicate pain areas on the three-dimensional hand model and to annotate types (e.g., sharp, dull, numb, throbbing, aching, pain only with movement, pain increase with movement) and magnitudes of pain at each pain area; prompt the user to indicate areas of swelling on the three-dimensional hand model; and/or prompt the user to indicate areas of reduced mobility on the three-dimensional hand model, such as reduction in range of motion in rotation of the forearm, articulation of the wrist, and articulation of each finger. For example, the native application can: render the three-dimensional hand model on the display of the computing device; enable the user to place markers on discrete locations and over areas of the three-dimensional hand model; open a menu of pain, swelling, and mobility options for each marker; and annotate each marker with pain, swelling, and/or mobility tags selected by the user, such as described above.

In another implementation, the native application can receive injury data for the target hand of the patient on the three-dimensional hand model at the computing device by rendering the three-dimensional hand model on a display of the computing device; receiving user input defining a set of markers on the three-dimensional hand model via the display of the computing device; displaying an annotation menu of injury data for each marker; and, for each marker in the set of markers, receiving a selection of an annotation from the annotation menu via the display of the computing device.

Additionally or alternatively, the native application can prompt the user to complete a textual or graphical survey for presence and magnitude of pain, swelling, and mobility reduction throughout the target hand and forearm.

6.3 Diagnosis

The native application (or the remote computer system) can then insert locations of pain areas, pain types, pain magnitudes, swelling, and/or mobility loss, etc. into a diagnosis model, which returns a prediction for a particular type (and magnitude) of the injury to the user's hand.

Alternatively, for each pain area indicated by the user, the native application (or the remote computer system) can: identify a region of the target hand cospatial with the indicated pain area; query an injury table for an injury type that occurs in this hand region and yields a pain type indicated in this hand region; store the injury type returned by the injury table as a predicted injury type for the target hand; and predict a magnitude of the injury type based on medical history and pain magnitude indicated in this hand region by the user.

In another implementation, the native application (or the remote computer system) can predict the injury type based on injury data (e.g., input by the user via the native application) by: identifying a region of the target hand corresponding to a user annotation defining a pain area and a pain magnitude; querying an injury table for an injury type that corresponds to the region; storing the injury type returned by the injury table as a predicted injury type for the target hand; and predicting a magnitude of the injury type based on a medical history of the patient and the pain magnitude.

However, the native application (and/or the remote computer system) can implement any other method or technique to automatically predict an injury type (or a combination of injury types, an injury magnitude, etc.) to the target hand based on medical history and symptoms reported by the user (e.g., in person with the user or during a tele-health session).

6.4 Brace Model

The native application (or the remote computer system) can then generate a custom hand brace model for the target hand of the patient.

6.4.1 Template Brace Model

In one implementation, the native application (or the remote computer system) can select a hand brace type linked to the predicted injury type for the target hand of the patient.

Alternatively, in the variation described above in which the remote computer system generates a brace type model, the native application (or the remote computer system) can insert injury symptoms reported by the user into the hand brace model, which returns identification of a particular brace type, a configuration of the particular hand brace type, and/or a boundary profile for the particular hand brace predicted to address the user's symptoms.

The native application can then: retrieve a description and/or a graphical representation (e.g., an image, a video) of the particular hand brace type; present the predicted injury type, the description of the particular hand brace type, and/or the graphical representation of the particular hand brace type to the user for confirmation; and prompt the user to confirm creation and provision of a custom hand brace of this particular type, configuration, etc. for the user.

If the user confirms creation and provision of the custom hand brace, the native application (or the remote computer system) can implement methods and techniques as described above to: retrieve a template brace model of the particular brace type (such as including a three-dimensional model of the particular brace type, a specification for a type of brace material); deform the interior surface of the template brace model into alignment with the exterior surface of the three-dimensional hand model based on the predicted injury type; project a boundary profile onto the deformed template brace model; retract or extend the deformed template brace model to this boundary profile; store the resulting deformed template brace model as a custom hand brace model for the user; and render the custom hand brace model for review by the user.

6.4.2 Custom-Generated Brace Model

In another implementation, the native application (or the remote computer system) can derive an initial hand brace model from the three-dimensional hand model of the patient (rather than retrieving a template brace model) and customize the initial hand brace model to generate the custom brace for the patient.

The native application (or the remote computer system) can implement methods and techniques described herein to generate a custom hand brace model at the computing device by: extracting a first set of points from the three-dimensional hand model for the patient to generate an initial hand brace model; forming an interior surface of the initial hand brace model based on the first set of points; and deforming the interior surface of the initial hand brace model into alignment with an exterior surface of the three-dimensional hand model to generate the custom hand brace model.

6.5 Custom Brace Confirmation

The native application can implement methods and techniques described herein to render the custom hand brace model for review by the user and prompt the user to confirm production of a custom hand brace for the patient according to this custom hand brace model, as shown in FIG. 1.

The remote computer system (or the native application) can also: estimate a print time to create a custom hand brace based on the custom hand brace model; estimate a cost to fabricate the custom hand brace based on the print time and a size (e.g., length and/or volume) of the custom hand brace; and predict a delivery time for the custom hand brace based on a shipping address of the patient, the print time, and a predefined assembly time for the custom hand brace. The native application (and/or the remote computer system) can then: present the estimated cost and/or predicted delivery time on a display of the computing device; transmit a prompt to confirm an order for the custom hand brace via the display of the computing device; in response to receiving confirmation of the order, queue a three-dimensional printer to print the custom hand brace based on the custom hand brace model, as shown in FIG. 1; and queue the resulting custom hand brace for assembly and delivery to the patient.

In another implementation, the native application can render the custom hand brace model for review and transmit a prompt to confirm production of a custom hand brace for the patient at an advanced manufacturing system located within a clinic and/or store at which the patient is being evaluated, such that the patient can receive the custom hand brace before leaving the clinic and/or store. More specifically, the remote computer system (or the native application) can: estimate a print time to create a custom hand brace based on the custom hand brace model; estimate a cost to fabricate the custom hand brace based on the print time and a size (e.g., length and/or volume) of the custom hand brace; present the estimated cost on a display of the computing device; transmit a prompt to confirm an order for the custom hand brace via the display of the computing device; in response to receiving confirmation of the order, queue a three-dimensional printer to print the custom hand brace based on the custom hand brace model, as shown in FIG. 1; and queue the resulting custom hand brace for assembly for the patient.

7. Generic Hand Brace

In another configuration, the native application (and/or the remote computer system) can implement similar methods and techniques to support the user in selecting and adjusting a generic hand brace according to the user's self-reported pain, swelling, and/or mobility symptoms.

7.1 Generic Hand Brace Guide

In this configuration, a "generic" brace may be available in a small number of different sizes (e.g., small, medium, large)—such as stocked at a pharmacy—each configured to be "customized" for various hand, wrist, and forearm injuries of users within a small number of (e.g., three) hand size ranges.

In one implementation, a generic brace: includes one contiguous structure with integrated peripheral extensions, such as a thumb brace, a radial gutter support, and an ulnar gutter brace located on the extended wrist and forearm brace; and is constructed from one or more layers of polymer and/or textile and configured to be trimmed with scissors or shears.

In another implementation, a generic brace includes: a core brace structure; and separable peripheral extensions—such as including a thumb brace, a radial gutter support, an ulnar gutter brace, forearm extension—assemblable onto the core brace structure (e.g., via hook-and-loop connectors) and/or configured to be trimmed with scissors or shears to customize the generic hand brace for a user's unique physiology.

7.2 Setup

In one example, a user injures her hand (i.e., the target hand) and then visits a pharmacy that stocks the set of generic braces. Upon viewing these generic hand braces on a shelf in the pharmacy, the user scans a code (e.g., a QR code) on a package of a generic brace with her computing device, which triggers installation of the native application on her computing device, or otherwise downloads the native application to her computing device according to instructions on the package of the generic hand brace.

7.3 Scan and Three-Dimensional Hand Model

The user then opens the native application on her computing device, which guides the user in scanning her target hand, as described above. The native application (and/or the remote computer system) then: generates a three-dimensional model of the target based on data captured during this scan, as described above; extracts a set of feature dimensions of the target from the three-dimensional model, such as a width of the styloid processes, a length of the forearm, a width of the palm, a distance from a line through the metacarpophalangeal joints to a line through the styloid processes, and/or lengths of the phalanges; and identifies a particular size—in the set of available sizes of the generic hand brace—nearest the size of the target hand, such as by identifying a particular size of the generic hand brace associated with a set of features ranges that include (all or the greatest number of) the set of feature dimensions extracted from the three-dimensional hand model.

7.4 Diagnosis

The native application can then: render the three-dimensional hand model on the display of the computing device; prompt the user to annotate the three-dimensional hand model with pain areas on the three-dimensional hand model and to annotate types (e.g., sharp, dull, numb, throbbing, aching, pain only with movement, pain increase with movement) and magnitudes of pain at each pain area; prompt the user to indicate areas of swelling on the three-dimensional hand model; and/or prompt the user to indicate areas of reduced mobility on the three-dimensional hand model, such as reduction in range of motion in rotation of the forearm, articulation of the wrist, and articulation of each finger. Additionally or alternatively, the native application can prompt the user to complete a textual or graphical survey for presence and magnitude of pain, swelling, and/or mobility reduction throughout the target hand and forearm.

The native application (or the remote computer system) can then insert locations of pain areas, pain types, pain magnitudes, swelling, and/or mobility reduction into the diagnosis model, which returns a prediction for a particular type (and magnitude) of the injury to the user's hand, such as described above. Additionally or alternatively, for each indicated pain area, the native application (and/or the remote computer system) can: identify a region of the target hand cospatial with the indicated pain area; query an injury table for an injury type that occurs in this hand region and yields a pain type indicated in this hand region; store the injury type returned by the injury table as a predicted injury type for the target hand; and predict a magnitude of the injury type based on the pain magnitude indicated in this hand region by the user.

However, the native application and/or the remote computer system can implement any other method or technique to predict an injury type to the target hand based on self-reported pain, swelling, and/or mobility loss reported by the user.

7.5 Generic Hand Brace Recommendation

The native application (or the remote computer system) can then confirm that the generic hand brace is configurable for the predicted injury type, such as by verifying that a list of injury types supported by the generic hand brace includes the injury type predicted for the user.

If this predicted injury type is supported by the generic hand brace, the native application can prompt the user to acquire the generic hand brace in the particular size predicted to best fit the user.

7.6 Generic Hand Brace Setup Guidance

Then, in response to the user confirming acquisition of the generic hand brace in the particular size, the native application (or the remote computer system) can generate guidance for customizing the generic hand brace for the user's injury.

For example, in the implementation described above in which the generic hand brace includes a core brace structure and a set of separable peripheral extensions, the native application (or the remote computer system) can: retrieve a configuration specification for supporting the predicted injury type with the generic hand brace, such as in the form of textual instructions and/or a graphic indicating inclusion and omission of select peripheral extensions; present the configuration specification to the user; and prompt the user to configure the generic hand brace according to this configuration specification.

For example, in the implementation described above in which the core brace structure and/or the separable peripheral extensions of the generic hand brace are configured to be trimmed with scissors or shears, the native application (or the remote computer system) can: retrieve a virtual template brace model of the generic hand brace configured with a (sub)set of separable peripheral extensions and defining a boundary profile associated with the predicted injury type; implement methods and techniques described above to locate the template brace model over the three-dimensional hand model, such as by aligning snap points defined in the template brace model to corresponding key features detected in the three-dimensional hand model; and deform the template brace model to locate the interior surface of the template brace model into contact with the surface of the three-dimensional hand model. The native application can then render the resulting "customized" brace model on the display of the computing device with a prompt for the user to: locate the peripheral extensions indicated in the custom hand brace model on the core brace structure of the generic hand brace; and trim (i.e., cut) the peripheral extensions and/or the core brace structure of the generic hand brace according to the boundary profile depicted in the custom hand brace model.

In another example, in the implementation described above in which the core brace structure and peripheral extensions of the generic hand brace are integrated and configured to be trimmed with scissors or shears, the native application (or the remote computer system) can: retrieve a virtual template brace model of the generic hand brace trimmed to a particular boundary profile according to the predicted injury type; implement methods and techniques described above to locate the template brace model over the three-dimensional hand model, such as based on snap points defined in the template brace model and key features detected in the three-dimensional hand model; and then deform the remainder of the template brace model to locate the interior surface of the template brace model into contact with the surface of the three-dimensional hand model. The native application can then render the resulting "customized" brace model on the display of the computing device with a prompt for the user to trim (i.e., cut) the generic hand brace according to the boundary profile depicted in the custom hand brace model.

The native application can therefore implement a template brace model of the generic hand brace and the three-dimensional model of the user's hand to calculate a set of configurations and/or adjustments to the generic hand brace in order to customize the generic hand brace for the user's physiology and for the injury to the user's hand.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or computing device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

I claim:

1. A computer-based method for generating a custom body part brace for a patient, the method comprising:
    compiling optical data captured during a three-dimensional scan of a target body part of the patient into a three-dimensional body part model of the target body part at a computing device;
    receiving condition data for the target body part of the patient on the three-dimensional body part model at the computing device comprising:
        rendering the three-dimensional body part model on a display of the computing device;
        receiving user input defining a set of markers on the three-dimensional body part model via the display of the computing device;
        displaying an annotation menu of condition data for each marker; and
        for each marker in the set of markers, receiving a selection of an annotation from the annotation menu via the display of the computing device;
    predicting a condition type based on the condition data at the computing device;
    retrieving a body part brace type, from a set of body part brace types, based on the condition type at the computing device;
    retrieving a template brace model for the body part brace type at the computing device;
    overlaying the template brace model onto the three-dimensional body part model at the computing device; and
    deforming the template brace model into alignment with the three-dimensional body part model to calculate a custom body part brace model at the computing device.

2. The method of claim 1, wherein compiling optical data captured during the three-dimensional scan of the target body part of the patient into the three-dimensional body part model of the target body part further comprises:
    rendering the three-dimensional body part model on the display of the computing device; and
    for each key feature in a set of key features on the three-dimensional body part model:
        transmitting a prompt on the display of the computing device to label a key feature on the three-dimensional body part model;
        receiving a selection of a pixel location on the three-dimensional body part model via the display of the computing device; and
        storing the pixel location on the three-dimensional body part model as corresponding to the key feature.

3. The method of claim 1, wherein predicting the condition type based on the condition data comprises:
    identifying a region of the target body part corresponding to a user annotation defining a pain area and a pain magnitude;
    querying an condition table for the condition type that corresponds to the region;
    storing the condition type returned by the condition table as a predicted condition type for the target body part; and
    predicting a magnitude of the condition type based on a medical history of the patient and the pain magnitude.

4. The method of claim 1, wherein deforming the template brace model into alignment with the three-dimensional body part model to calculate the custom body part brace model comprises deforming an interior surface of the template brace model into alignment with an exterior surface of the three-dimensional body part model based on the predicted condition type.

5. The method of claim 1, wherein deforming the template brace model into alignment with the three-dimensional body part model to calculate the custom body part brace model comprises:
    rendering the template brace model overlaid onto the three-dimensional body part model on the display of the computing device;
    rendering a virtual slider along a length of the body part and a corresponding section on the template brace model on the display of the computing device;
    rendering a virtual pointer on the virtual slider on the display of the computing device;
    in response to user input adjusting a position of the virtual pointer along the virtual slider, adjusting a length of the corresponding section on the template brace model; and
    storing the adjusted body part brace model as the custom body part brace model.

6. The method of claim 1, wherein calculating the custom body part brace model at the computing device further comprises:
    rendering the template brace model overlaid onto the three-dimensional body part model on the display of the computing device;
    receiving a selection of a pixel location on the template brace model via the display of the computing device;
    receiving an annotation defining an aperture at the pixel location on the template brace model via the display of the computing device;
    updating the template brace model to define the aperture at the pixel location; and
    storing the updated template body part brace model as the custom body part brace model.

7. The method of claim 1, further comprising queuing, at the computing device, the custom body part brace model for fabricating at an advanced manufacturing system.

8. The method of claim 7:
further comprising:
estimating a print time to fabricate the custom body part brace based on the custom body part brace model;
estimating a cost to fabricate the custom body part brace based on the print time and a size of the custom body part brace;
presenting the estimated cost on the display of the computing device; and
transmitting a prompt to confirm an order for the custom body part brace via the display of the computing device; and
wherein queuing the custom body part brace model comprises, in response to receiving confirmation of the order, queuing a three-dimensional printer to print the custom body part brace based on the custom body part brace model.

9. The method of claim 1, wherein the target body part includes one of a hand, an arm, a back, an ankle, or a neck.

10. A computer-based method for generating a custom body part brace for a patient, the method comprising:
retrieving a three-dimensional body part model of a target body part of the patient at a computing device;
receiving condition data for the target body part of the patient on the three-dimensional body part model at the computing device comprising:
rendering the three-dimensional body part model on a display of the computing device;
receiving user input defining a set of markers on the three-dimensional body part model via the display of the computing device;
displaying an annotation menu of condition data for each marker; and
for each marker in the set of markers, receiving a selection of an annotation from the annotation menu via the display of the computing device;
predicting a condition type based on the condition data at the computing device; and
based on the predicted condition type, generating a custom body part brace model at the computing device by:
automatically extracting a first set of points from the three-dimensional body part model to generate an initial body part brace model;
forming an interior surface of the initial body part brace model based on the first set of points; and
deforming the interior surface of the initial body part brace model into alignment with an exterior surface of the three-dimensional body part model to generate the custom body part brace model.

11. The method of claim 10, wherein generating the custom body part brace model at the computing device further comprises:
rendering the initial body part brace model overlaid onto the three-dimensional body part model on the display of the computing device;
rendering a virtual slider along a length of the body part and a corresponding section on the initial body part brace model;
rendering a virtual pointer on the virtual slider;
in response to user input adjusting a position of the virtual pointer along the virtual slider, adjusting a length of the corresponding section on the initial body part brace model; and
storing the adjusted body part brace model as the custom body part brace model.

12. The method of claim 10, wherein generating the custom body part brace model at the computing device further comprises:
rendering the initial body part brace model overlaid onto the three-dimensional body part model on the display of the computing device;
receiving a selection of a pixel location on the initial body part brace model via the display of the computing device;
receiving an annotation defining an aperture at the pixel location on the initial body part brace model via the display of the computing device;
updating the initial body part brace model to define the aperture at the pixel location; and
storing the updated initial body part brace model as the custom body part brace model.

13. The method of claim 10, further comprising queuing, at the computing device, the custom body part brace model for fabricating at an advanced manufacturing system.

14. The method of claim 13, further comprising:
estimating a print time to fabricate the custom body part brace based on the custom body part brace model;
estimating a cost to fabricate the custom body part brace based on the print time and a size of the custom body part brace;
presenting the estimated cost on the display of the computing device; and
transmitting a prompt to confirm an order for the custom body part brace via the display of the computing device; and
wherein queuing the custom body part brace model comprises, in response to receiving confirmation of the order via the display of the computing device, queueing a three-dimensional printer to print the custom body part brace based on the custom body part brace model.

15. The method of claim 10, wherein the body part includes one of a hand, an arm, a back, an ankle, or a neck.

16. A method, comprising:
generating a custom body part brace, wherein generating the custom body part brace includes:
retrieving, by one or more processors, a three-dimensional body part model of a target body part;
receiving, by the one or more processors, condition data for the target body part of the patient on the three-dimensional body part model; and
generating, by the one or more processors based on a predicted condition type, the custom body part brace model, wherein generating the custom body part brace model further includes:
automatically extracting, by the one or more processors, a first set of points from the three-dimensional body part model to generate an initial body part brace model;
forming, by the one or more processors, an interior surface of the initial body part brace model based on the first set of points; and
deforming, by the one or more processors, the interior surface of the initial body part brace model into alignment with an exterior surface of the three-dimensional body part model to generate the custom body part brace model;
estimating, by the one or more processors, a print time to fabricate a custom body part brace based on a custom body part brace model;

estimating, by the one or more processors, a cost to fabricate the custom body part brace based on the print time and a size of the custom body part brace;

presenting, by the one or more processors, the estimated cost on a display of a device; and transmitting, by the one or more processors, a prompt to confirm an order for the custom body part brace via the display; and queuing, by the one or more processors, the custom body part brace model for fabricating at an advanced manufacturing system.

17. The method of claim 16, wherein queuing the custom body part brace model comprises, in response to receiving confirmation of the order, queueing, by the one or more processors, a three-dimensional printer to print the custom body part brace based on the custom body part brace model.

18. The method of claim 16, wherein receiving the condition data comprises:

rendering, by the one or more processors, the three-dimensional body part model on the display;

receiving, by the one or more processors, user input defining a set of markers on the three-dimensional body part model;

displaying, by the one or more processors, an annotation menu of condition data for each marker;

for each marker in the set of markers, receiving, by the one or more processors, a selection of an annotation from the annotation menu; and predicting, by the one or more processors based on the condition data, the condition type.

* * * * *